| United States Patent [19] | [11] Patent Number: 5,008,247 |
| Meinetsberger | [45] Date of Patent: Apr. 16, 1991 |

[54] POLYSULFURIC ACID ESTERS OF BIS-ALDONAMIDES AND THEIR DERIVATIVES, PROCESS FOR THEIR PREPARATION AND MEDICAMENTS

[75] Inventor: Eike Meinetsberger, Munich, Fed. Rep. of Germany

[73] Assignee: Luitpold-Werk Chemisch-pharmazeutische Fabrik GmbH & Co., Munich, Fed. Rep. of Germany

[21] Appl. No.: 256,624

[22] Filed: Oct. 12, 1988

[30] Foreign Application Priority Data

Oct. 14, 1987 [DE] Fed. Rep. of Germany ....... 3734815

[51] Int. Cl.$^5$ ..................... C07H 15/04; C07H 15/18; C07H 11/00; A61K 31/72
[52] U.S. Cl. ......................................... 514/23; 514/25; 536/1.1; 536/53; 536/54; 536/116; 536/118
[58] Field of Search .................. 536/116, 118, 54, 53, 536/1.1; 514/23, 25

[56] References Cited

U.S. PATENT DOCUMENTS 4,229,446 10/1980 Takemoto et al. .................. 514/159
4,357,326 11/1982 Nair et al. ............................. 536/118
4,587,250 5/1986 Klauser et al. ....................... 514/278

OTHER PUBLICATIONS

"Synthesis of a New Class of Model Glycolipids" (Dep. Biol. Chem., Univ. of Mich.; Ann Arbor, Mich.), Carbohydr. Res., 1978, 67(1), C1–C3.
"A New Class of Nonionic Detergents with a Gluconomide Polar Group" (Lab. Vision Res., Natl. Eye Inst., Bethesda, Md.), Anal. Biochem., 1983, 130(2), 485–90.
"Affects of Nonionic Contracts Media on the Components of Coagulation and Complement Systems" (Med. Cent., Loyola Univ., Maywood, Ill.), Invest. Radiol., 1983, 18(3), 279–84.

*Primary Examiner*—Ronald W. Griffin
*Attorney, Agent, or Firm*—Burns, Doane, Swecker & Mathis

[57] ABSTRACT

The invention relates to polysulfuric acid esters of bis-aldonamides in which the underlying aldonic acids can be linked glycosidically with a galactopyranosyl, mannopyranosyl, glucopyranosyl or oligopyranosyl radical in the 3-, 4- or 6-position. They are therapeutically active compounds, whose preparation and pharmaceutical compositions are likewise described.

17 Claims, No Drawings

POLYSULFURIC ACID ESTERS OF BIS-ALDONAMIDES AND THEIR DERIVATIVES, PROCESS FOR THEIR PREPARATION AND MEDICAMENTS

DESCRIPTION

The invention relates to polysulfuric acid esters of bis-aldonamides and their derivatives of the general formula I,

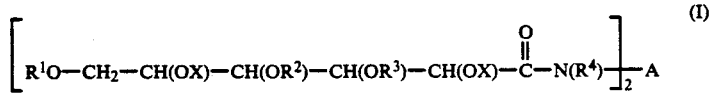

in which either all radicals $R^1$, $R^2$ and $R^3$ independently of one another stand for X, or two of the radicals $R^1$, $R^2$ and $R^3$ stand for X, and the third stands for a radical of the formulae II–VII,

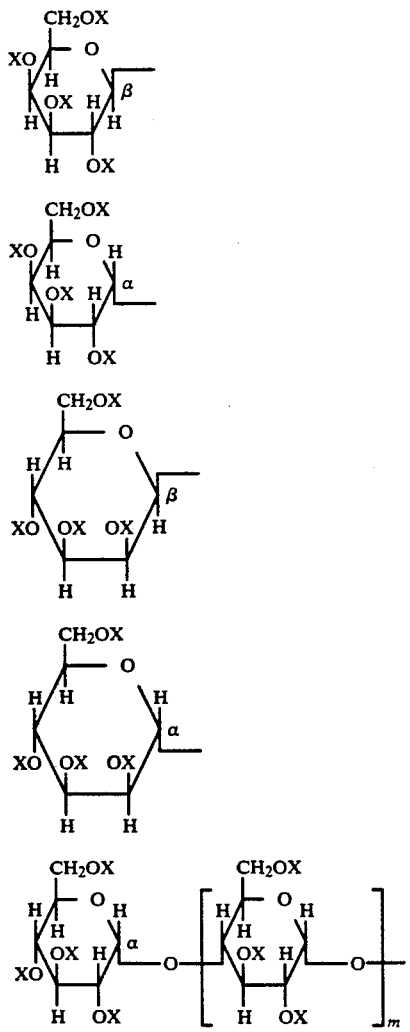

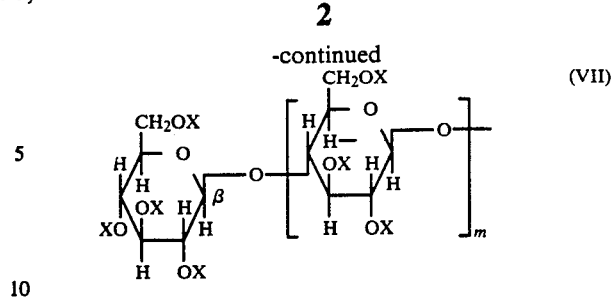

X in the formulae I to VII simultaneously or independently of one another denotes a hydrogen atom or the group —$SO_3H$, where at least one X stands for the group —$SO_3H$, m stands for 0, 1, 2, 3, 4, 5 or 6, A in formula I stands for a straight-chain or branched, saturated alkylene radical having 2 to 22 carbon atoms which is optionally substituted by one or more radicals —$CO_2R^5$, and this alkylene radical is optionally interrupted by up to 5 —O—, —S—, —S—S—, —$S(O)_n$—,

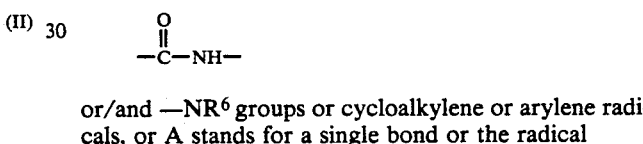

or/and —$NR^6$ groups or cycloalkylene or arylene radicals, or A stands for a single bond or the radical

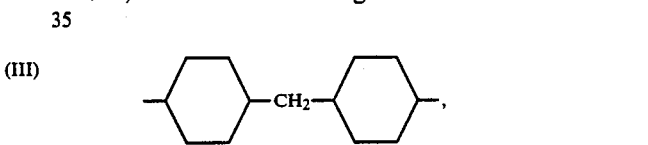

n is 1 or 2, $R^4$, $R^5$ and $R^6$ simultaneously or independently of one another denote a hydrogen atom or a $C_1$–$C_6$-alkyl radical, and their salts with inorganic or organic bases.

The compounds according to the invention represent active compounds having useful pharmacological properties, as is shown below.

The following comments apply to the various substituents or radicals (in the various formulae indicated) mentioned in connection with the present invention:

The aldonic acids underlying the present polysulfuric acid esters possess the general formula VIII

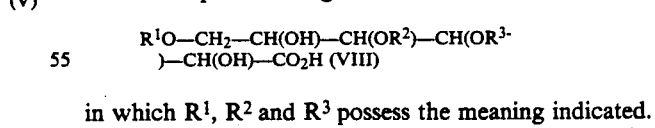

in which $R^1$, $R^2$ and $R^3$ possess the meaning indicated. These aldonic acids can be present in the D-form, the L-form or in the form of their racemates, preferably in their naturally predominant form.

Examples of these aldonic acids comprise the hexonic acids allonic acid, altronic acid, galactonic acid, gluconic acid, gulonic acid, idonic acid, mannonic acid and talonic acid, preferably galactonic acid, gluconic acid, gulonic acid and mannonic acid. Further examples are derivatives of these hexonic acids which are connected glycosidically on the oxygen atoms in the 3-, 4-, or 6-position with a radical $R^3$ or $R^2$ or R1 of the formulae II to VII, in which X stands for hydrogen. The bond here can be α- or β-glycosidic. The radicals II to V are galactopyranosyl and mannopyranosyl radicals. The radicals VI and VII are glucopyranosyl radicals (in the case where m=0) and α(1→4) or β(1→4)-linked oligoglucopyranosyl radicals (when m=1 to 6). The index m in the formulae VI and VII preferably stands for 0 or 1. The saccharide units linked with the aldonic acid are normally present in the D-form. Examples of hexonic acids of the general formula VIII which are substituted with radicals of the formulae II to VII are glucopyranosylgluconic acids, glucopyranosylmannonic acids, glucopyranosylgalactonic acids, galactopyranosylgluconic acids, mannopyranosylgluconic acids, mannopyranosylmannonic acids and oligoglucopyranosylgluconic acids. Lactobionic acid (4-O-β-D-galactopyranosylgluconic acid), gentiobionic acid, melibionic acid (6-O-α-D-galactopyranosylgluconic acid), mannobionic acid, cellobionic acid (4-O-β-D-glucopyranosylgluconic acid) and maltobionic acid (4-O-α-D-glucopyranosylgluconic acid) and also maltotrionic acid and cellotrionic acid are preferred here.

Examples of salt-forming bases are trialkylamines having 1 to 6 carbon atoms in the alkyl moiety, such as trimethylamine, triethylamine, tripropylamine, tributylamine, tripentylamine and trihexylamine. Trimethylamine, triethylamine and tributylamine are preferred.

Examples of physiologically tolerable inorganic and organic salts are the ammonium, lithium, sodium, potassium, magnesium, calcium and aluminum salts and the salts with ethanolamine, triethanolamine, morpholine, pyridine and piperidine. The sodium, potassium, calcium, aluminum and ethanolamine salts are preferred.

Examples of the straight-chain or branched, saturated alkylene radicals having 2 to 22 carbon atoms representing the group A are ethylene, tri-, tetra-, penta-, hexa-, hepta-, octa-, nona-, deca-, undeca-, dodeca-, tetradeca-, hexadeca-, octadeca-, icosa- and docosamethylene and also methylethylene, methylpropylene, methylbutylene, methylpentylene and dimethylethylene. Ethylene, tri-, tetra-, hexa-, nona-, dodeca- and docosamethylene and also methylethylene and methylpentylene are preferred.

Examples of arylene radicals by which the alkylene radical of the group A can be interrupted are phenylene, naphthylene, anthrylene, phenanthrylenes and fluorenylenes. In this connection, ortho-, meta- and para-phenylene radicals are preferred.

Examples of cycloalkylene radicals by which the alkylene radical of the group A can be interrupted are cyclopentylene, cyclohexylene, cycloheptylene and cyclooctylene, 1,3- and 1,4-cyclohexylene being preferred here.

The straight-chain or branched, saturated lene radical of the group A preferably possesses 2 to 12 carbon atoms. If the straight-chain or branched, saturated alkylene radical of the group A is interrupted by one of the radicals or groups mentioned, it is preferably 1 or 2 of those radicals or groups.

Specific examples of alkylene radicals representing group A according to the definition are groups derived from the following α,ω-diamines:

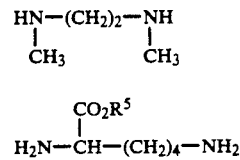

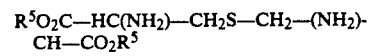

Enantiomers of lysine ($R^5=H$) and its esters ($R^5=C_1-C_6$-alkyl) containing S atoms:

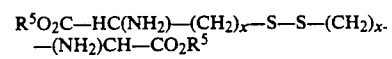

Diastereomers of lanthionine ($R^5=H$) and esters ($R^5=C_1-C_6$-alkyl)

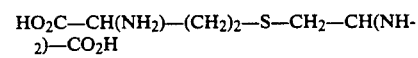

Diastereomers of cystine (x=1, $R^5=H$) and esters ($R^5=C_1-C_6$-alkyl)

Diastereomers of homocystine (x=2, $R^5=H$) and esters ($R^5=C_1-C_6$-alkyl)

$$HO_2C-CH(NH_2)-(CH_2)_2-S-CH_2-CH(NH_2)-CO_2H$$

Diastereomers of cystathionine

| containing NH groups: | |
|---|---|
| $H_2N-(CH_2-CH_2-NH)_x-CH_2-CH_2-NH_2$ | x = 1 diethylenetriamine |
| | x = 2 triethylenetetramine |
| | x = 3 tetraethylenepentamine |
| $H_2N-(CH_2)_2-NH-(CH_2)_3-NH-(CH_2)_2-NH_2$ | 1,9-diamino-3,7-diazanonane |
| $H_2N-(CH_2)_3-NH-)CH_2)_2-NH-(CH_2)_3-NH_2$ | 1,10-diamino-4,7-diazadecane |
| $H_2N-(CH_2)_6-NH-(CH_2)_6-NH_2$ | bis-(6-aminohexyl)amine |
| $H_2N-(CH_2)_3-NH-(CH_2)_4-NH-(CH_2)_3-NH_2$ | spermine |
| $H_2N-(CH_2)_4-NH-(CH_2)_3-NH_2$ | spermidine |
| $H_2N-(CH_2)_3-NH-(CH_2)_3-NH-(CH_2)_3-NH_2$ | 1,11-diamino-4,8-diazaundecane |
| containing O atoms: | |
| $H_2N-(CH_2)_2-O-(CH_2)_2-NH_2$ | bis-(2-aminoethyl) ether |

The group A can preferably stand for the following radicals:

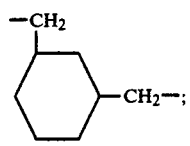

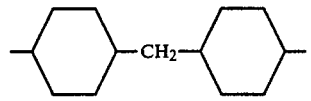

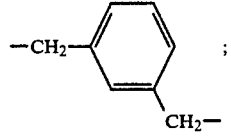

-continued

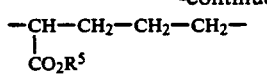

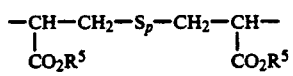

having p = 1 or 2
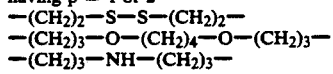

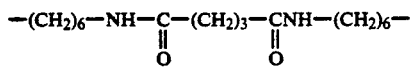

Examples of $C_1$-$C_6$-alkyl radicals of the groups $R^4$, $R^5$ and $R^6$ are methyl, ethyl, n-propyl, n-butyl, n-pentyl, n-hexyl, isopropyl, isobutyl, tert.-butyl, neopentyl, whereby methyl, ethyl, n-propyl, isoprooyl, tert.-butyl and n-butyl are preferred.

The invention also relates to a process for the preparation of polysulfuric acid esters of bis-aldonamides of the general formula I, which comprises reacting bis-aldonamides of the general formula IX

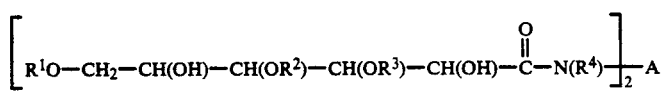

in which $R^1$, $R^2$, $R^3$, $R^4$ and A have the meanings indicated, where, however, X in the formulae II to VII stands for hydrogen, with a sulfating agent in an aprotic solvent and converting the products thus obtained into the correpsonding salts using an inorganic or organic base. The compounds of the general formula IX are obtained in analogy to processes known from the literature (for example: F. Scholnick, P. E. Pfeffer, J. Dairy Sci. 63 (3), 471 (1980); W. N. Emmerling, B. Pfannemüller, Starch 33 (6), 202 (1981)). To prepare the bis-aldonamides of the general formula IX, lactones of the aldonic acids of the general formula VIII are allowed to react in a solvent with a diamino compound $R^4HN$—A—$NHR^4$. The lactones can be employed both in the 1,4-lactone form of the general formula X and also in the 1,5-lactone form of the general formula XI.

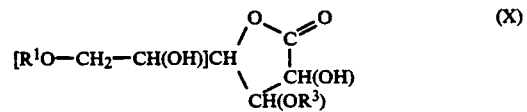

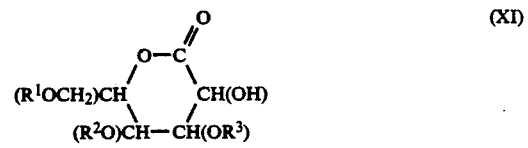

The compounds of the general formulae X and XI are obtained by elimination of water from the aldonic acids VIII. The aldonic acids can be obtained by processes known from the literature (for example W. N. Emmerling, B. Pfannemüller, Starch 33 (6), 202 (1981); R. Schaffer, H. S. Isbell, J. Am. Chem. Soc. 81, 2178 (1959), H. W. Diehl et al., Carbohydrate Research 38, 364 (1974)) by electrochemical or hypohalite oxidation of the corresponding aldoses. To prepare the bis-aldonamIdes of the general formula IX, 2 moles of aldonolactone are employed per mole of diamino compound. Suitable solvents for the reaction are methanol, ethanol, ethylene glycol, dimethyl sulfoxide, dimethylformamide or N-methylpyrrolidone. Dimethylformamide is preferred. The reaction times are several hours to days, preferably between 5 and 8 h. The reaction temperatures are between room temperature and the boiling temperatures of the respective solvents, preferably between 40° C. and 80° C. The aldonic acid amides either crystallize out of the reaction solution or can be precipitated by addition of an organic solvent. Suitable for this are methanol, ethanol, isopropanol or acetone, preferably isopropanol.

The aldonamide(s) of the general formula IX are the subject of German Patent Application P 37 34 853.1 from the same Applicant of the same application date (case BAA, title "Aldonamide(s) and process for their preparation"), whose disclosure shall presently be embraced in addition by way of reference.

To prepare the present compounds of the general formula I, the aldonamide(s) of the formula IX are dissolved or suspended in an aprotic solvent. Pyridine, dimethylformamide, dimethylacetamide, N-methylpyrrolidone etc. are suitable, dimethylformamide being preferred.

The mixture is heated to temperatures between 20° C. and 100° C., preferably between 30° C. and 70° C., and a sulfating agent is added. Examples of this are chlorosulfonic acids, sulfur trioxide, oleum, or ether- or amine-sulfur trioxide complexes. Sulfur trioxide complexes with trimethylamine, triethylamine and pyridine are preferably employed.

In order to obtain polysulfuric acid esters of bis-aldonamides of the general formula I, in which each X stands for the group —$SO_3H$, 1 to 2 equivalents of sulfating agent, preferably 1.4–1.7 equivalents, are employed for each hydroxyl group capable of esterification. Compounds in which some X are hydrogen atoms and the others are the group —$SO_3H$ are obtained when the sulfating agent is employed in subequivalent amounts. The amount of sulfating agent Is chosen depending on how high the sulfur content of the product should be. Amounts between 0.5 and 1 equivalent of sulfating agent per hydroxyl group capable of esterification are preferred. The reaction mixture is stirred for 1 to at temperatures between 20° C. and 100° C. From the polysulfate compounds of the general formula I thus obtained, in which X stands for —$SO_3H$, which can also be present as the salt of the amine of the amine-sulfur trioxide complex employed, the corresponding salts of inorganic bases are obtained by addition of these bases or their inorganic salts. The hydroxides and acetates of the alkali metals and alkaline earth metals are preferably employed here. Salts of physiologically acceptable organic bases are obtained either by using a sulfur trioxide complex of these bases in the sulfation reaction or by treating the alkaline earth metal salt or alkali metal salt with a cation exchanger in the acidic form and subsequently neutralizing the acidic sulfuric acid hemiester with the organic base. The isolation of the compounds according to the invention in general takes place by precipitating from the reaction solutions or from aqueous solutions using organic solvents. Suitable organic solvents are methanol, ethanol, isopropanol or acetone, preferably methanol.

The compounds can be purified by repeated precipitation from aqueous solutions using the abovementioned solvents and by treating with activated charcoal or hydrogen peroxide. In general, the products thus obtained are mixtures with a more or less high content of compounds, all the hydroxyl groups of which are esterified with sulfate radicals and of compounds whose hydroxyl groups are only partially sulfated, depending on the amount of sulfating agent employed. The mixtures obtained can optionally be separated into products having a uniform content of sulfate radicals by various separation processes. The separation may take place by various physical separation processes, such as, for example, fractional precipitation, gel chromatography, Ion exchange chromatography or affinity chromatography, HPLC or electrophoretic processes. Fractional precipitation is preferred. For example, an aqueous solution of the product mixture is prepared and one to four times the amount of an organic solvent is added. Watermiscible solvents such as methanol, ethanol, isopropanol, acetone or tetrahydrofuran are suitable, methanol being preferred. The precipitate thus obtained is allowed to settle. In general, the compounds having a higher sulfate content are then concentrated in the precipitate, and those having a lower sulfate content in the supernatant solution. Compounds having a defined number of sulfate groups are obtained by repeated fractional precipitation of the precipitates or supernatants.

In a preferred embodiment of the process according to the invention, the compounds of the formula I are produced from the aldonic acids of the formula VIII without isolation of the necessary intermediate.

In this connection, an aqueous solution of the free aldonic acids VIII is prepared by means of a cation exchanger from the alkali metal salts or alkaline earth metal salts of the aldonic acids VIII synthesized commercially or by processes known from the literature (for example W. N. Emmerling, B. Pfannemüller, Starch 33 (6), 202 (1981); R. Schaffer, H. S. Isbell, J. Am. Chem. Soc. 81, 2178 (1959), H. W. Diehl et al., Carbohydrate Research 38, 364 (1974)) and this is concentrated substantially. The lactones corresponding to the aldonic acids VIII are then produced in situ without isolation by elimination of water. For this purpose, the residue, which in general represents a water-containing mixture of aldonic acid and lactone, is dissolved in a high-boiling solvent. Examples of high-boiling solvents are dimethyl sulfoxide, dimethylformamide, N-methylpyrrolidone, dimethoxymethyl ether etc., dimethylformamide being preferred. A second, low-boiling solvent which can form an azeotrope with water is then added. Suitable solvents are, for example, n-pentane, n-hexane, cyclohexane, benzene, etc., n-hexane being preferred. Water is then eliminated quantitatively from the aldonic acids in a water separator. The low-boiling extraining agent is then distilled off and the lactone situated in the remaining, high-boiling solvent is reacted, without isolation of same, with the diamino compound. The reaction temperatures here are between 20° C. and 120° C., preferably between 50° C. and 80° C. The mixture is stirred over time spans of 3 to 24 hours, preferably 3 to 8 hours. Without isolation of the resulting bis-aldonamides this is brought to reaction with a sulfating agent in the same reaction vessel. Reaction conditions and isolation and purification of the products are described in the previously mentioned process.

The compounds of the general formula I are pharmacologically useful substances. They possess antithrombotic and anti-inflammatory properties. The compounds according to the invention are therefore suitable for the treatment of the whole circle of rheumatic diseases and for the prophylaxis and therapy of venous and arterial thrombosis. The invention therefore also relates to a medicament for human and veterinary use. Human use is preferred.

The antithrombotic activity of the compounds according to the invention is particularly surprising.

Up to now, heparin has primarily been used for prophylaxis of thrombosis. Heparin is a mucopolysaccharide which is isolated from animal tissue, in particular pig ileum (Thomas, D. P. (1981) in Clinics in Haematology, Vol. 10, p. 443–458, Saunders Comp. Ltd., 1981). In addition to heparin, other naturally occuring mucopolysaccharides, such as dermatan sulfate or heparan sulfate, also possess antithrombotic properties (Rosenberg, R. D., Rosenberg, J. S. (1984), J. Clin. Invest. 74, 1–6; Sie, P., Ofosu, F., Fernandez, F., Buchanan, M. R., Petitou, M., Boneu, B. (1986) Br. J. Haematol. 64, 707–714). A semi-synthetic chondroitin polysulfate is also known, for example from DE-PS 3,118,588, which, inter alia, has antithrombotic properties. However, only heparin is therapeutically used. More recently, several low molecular weight heparins have been developed for clinical use. In this case, they are substances which can be obtained from heparin by various chemical or enzymatic depolymerization processes (Thomas, D. P., Merton, R. E. (1982) Thrombos. Res. 28, 343–350; Walenga, J. M., Fareed, J., Petitou, M., Samana, M., Lormeau, J. C., Choay, J. (1986) Thrombos. Res. 43, 243–248; Koller, M., Schoh, U., Buchmann, P., Largiadèr, F., von Felten, A., Frick, P. G. (1986) Thrombos. Haemostas. 56, 243–246).

A disadvantage of the heparins and low molecular weight heparins is that they are of natural origin (for example derived from animals). There are therefore small amounts of antigen present derived from the animal tissue, which can lead to anaphylactic reactions such as a decrease in the number of thrombocytes, thrombosis and embolism. These side-effects are, of course, relatively rare, but can be serious and clinically difficult to control.

In contrast, the compounds according to the invention are wholly synthetic and therefore free of animal antigen.

Another substantially more frequent complication in the prophylaxis of thrombosis with heparin and low molecular weight heparin is the appearance of hemorrhages. Substances which cause less hemorrhages in combination with equivalent antithrombotic action can therefore represent a substantial therapeutic advance.

Several pharmacological tests were used to test the compounds according to the invention for antithrombotic activity and anti-inflammatory activity.

1. Acceleration of fibrinolysis

The formation of a clinically manifest (relatively large) thrombus can be prevented in various ways. For one, the factors which are involved in the formation of the primary thrombus, such as blood platelet aggregation or the blood clotting system, can be eliminated. On the other hand, the dissolution of the primary thrombus can be accelerated by potentiating endogeneous fibrinolysis. A potentiation of endogenous fibrinolysis can also serve to dissolve already clinically manifest thrombi again. The fibrinolytic action of a substance is thus of great significance in the prophylaxis and therapy of thrombosis. The fibrinolytic action of the substances according to the invention was determined in the test below. The test is a slight modification of a method known from the literature for the determination of fibrinolytic action (Kluft, C. (1979) Thromb. Haemostas. 41, 365–383).

Fibrinolysis test

Fibrinolysis was determined by means of plasminogen-containing fibrin plates.

Petri dishes, dia. 9 cm, were prewarmed to 40° C. 3 ml of a 2% solution of fibrinogen (Behringwerke, Marburg) in water, 1 ml of a plasminogen solution, 2 CTA/ml (Behringwerke, Marburg), 3 ml of a 1% agarose solution (Serva, Heidelberg) in 50 mM TRIS/HCl, pH 7.8 and 1 ml of a solution of 15 U/ml of thrombin (Behringwerke, Marburg) in water were pipetted into the dishes with swirling. After cooling the plates, wells of 5 mm diameter were punched out.

0.1 ml of plasma (human standard plasma, Behringwerke, Marburg), 0.8 ml of water and 0.1 ml of solution of the test substance in various concentrations were incubated for 10 minutes at 37° C. After addition of 0.9 ml of 0.025% acetic acid, the mixture was incubated for 5 minutes at 4° C. and subsequently centrifuged for 5 minutes at 2,000 g. The precipitate was taken up in 0.1 ml of buffer (20 mM TRIS/HCl, 100 mM NaCl, 2.7 mM EDTA, pH 7.8).

0.02 ml of this solution and 0.005 ml of 14.3 mM flufenamic acid solution (Sigma, Taufkirchen) in buffer are pipetted into the application wells of the fibrin plates. After 24 hours at 37° C., the lysis haloes were planimetered. The areas of the lysis haloes less the lysis areas without addition of substance serve as a measure for the fibrinolysis-increasing activity.

Result: The result is represented in the table below.

| Substance from Example | Fibrinolysis at 2 µg/ml (mm$^2$) |
|---|---|
| 23 | 21.6 |
| 20 | 19.2 |
| 24 | 17.8 |
| Heparin | 14.8 |

2. Inhibition of blood clotting

The inhibition of blood clotting can be measured in a simple manner by means of the activated partial thromboplastin time aPTT. It gives information about the general inhibition of the activated clotting system. In order to decrease the incidence of hemorrhages, as low as possible an inhibition of blood clotting is desired here. Clotting test, aPTT 0.1 ml of plasma and 0.1 ml of Pathromtin[R] (Behringwerke, Marburg) are incubated at 37° C. for 2 minutes and 0.1 ml of 25 mM CaCl$_2$ solution is added. The clotting time is measured in a Schnitger & Gross coagulometer. The agent is made up for 5 individual determinations per concentration. A heparin containing 175 U/mg from the firm Pharmindustrie is used as a standard.

The prlongation of the clotting time is converted into heparin units by means of a calibration curve. Since the calibration curves are not parallel, the prolongation of 150% of the blank vaue is chosen as the reference point.

Result: The following table shows the heparin units of compounds according to the invention.

| Substance from Example | u/mg |
|---|---|
| 23 | 30.9 |
| 25 | 5.85 |
| 20 | 42.1 |
| 24 | 14.1 |
| 31 | 10.2 |
| 34 | 15.1 |
| Heparin | 175 |
| Fragmin (low mol. wt. heparin) | 64.5 |

3. Influence on the bleeding time

A piece of tail about 2 mm long was cut from rats. The time until bleeding had stopped was measured. The test substance in various concentrations or physiological saline solution (control) was administered to the animals 5 minutes before causing the bleeding. Groups of 20 animals were treated. The proiongalion of the bleeding time compared to the control was expressed in percent.

| | Lengthening of the bleeding time (%) | | |
|---|---|---|---|
| | Dose (mg/kg) | | |
| Example | 0.25 | 0.5 | 2 |
| 20 | — | 5.1 | 35.1 |
| Heparin | 55.4 | 120 | |

4. Anti-inflammatory action

In inflammatory processes, large amounts of reactive oxygen species, among them superoxide radicals and hydroxyl radicals, are released from the phagocytes (polymorphonuclear leucocytes and macrophages). These radicals are involved in tissue destruction. Substances which inhibit the radical formation in leucocytes are therefore of great therapeutic interest in the control of inflammations (Flohé, L., Giertz, H., Beckmann, R. (1985) in The Pharmacology of inflammation, Vol. 5 (Bonta, I. et al. eds.) p. 255–281, Elsevier, Amsterdam-New York).

The radical formation by leucocytes can be measured by measuring the luminol-potentiated chemiluminescence in whole blood (Peter, M. et al. (1985) in Chi. Forum 85 (Stelzner, F., eds), p. 81–84, Springer Verlag, Berlin).

Test on anti-inflammatory action

Test substances are dissolved in PBS and serial dilutions are prepared in PBS. 600 µl of PBS, 100 µl of solution of the test substance, 100 µl of zymosan suspension (100 mg/ml) and 100 µl of citrated rabbit blood are pipetted into cuvettes which are suitable for a 1251 luminometer from LKB. The measurement is started by addition of 100 µl of $10^{-3}$M luminol solution. The chemiluminescence is measured every 5 minutes over 90 minutes in each sample. The maximum chemiluminescence is determined. A sample without test substance is used as a reference value. A sample without the addition of zymosan is used as a blank value. Three independent determinations are carried out per substance. The calculation of the residual chemiluminescence is performed according to the formula:

$$\frac{CL_{max}(\text{subst}) - CL_{max}(\text{blank})}{CL_{max}(\text{ref}) - CL_{max}(\text{blank})} \times 100$$

Concentrations for 50% CL inhibition ($IC_{50}$ values) result from a semilogarithmic plot of residual chemiluminescence against log concentration.

Result:

The inhibition of the luminol-potentiated CL by compounds according to the invention is shown in the table below.

| Substance from Example | $IC_{50}$ (µg/ml) |
|---|---|
| 23 | 225 |
| 25 | 155 |
| 20 | 540 |
| 24 | 220 |
| 31 | 170 |
| Indomethacin | 240 |

The present invention also relates to pharmaceutical preparations which contain one or more active compounds according to the invention or which consist of one or more active compounds according to the invention in addition to non-toxic, inert, pharmaceutically suitable excipients.

Non-toxic, inert, pharmaceutically suitable excipients are taken to mean solid, semi-solid or liquid diluents, fillers or formulation auxiliaries of any type.

Preferred pharmaceutical preparations which may be mentioned are tablets, dragees, capsules, pills, granules, suppositories, solutions, suspensions and emulsions, pastes, ointments, gels, creams, lotions, powders, sprays and aerosols.

Tablets, dragees, capsules, pills and granules may contain the active compound(s) in addition to the customary excipients, such as (a) fillers and extenders, for example starches, lactose, sucrose, glucose, mannitol and silica, (b) binders, for example carboxymethylcellulose, alginates, gelatin, polyvinylpyrrolidone, (c) humectants, for example glycerol, (d) disintegrants, for example agar-agar, calcium carbonate and sodium bicarbonate, (e) solution retardants, for example paraffin and (f) absorption accelerators, (g) wetting agents, for example cetyl alcohol, glycerol monostearate, (h) adsorption agents, for example kaolin and bentonite and (i) lubricants, for example talc, calcium stearate and magnesium stearate and solid polyethylene glycols or mixtures of the substances mentioned under (a) to (i).

The tablets, dragees, capsules, pills and granules may be provided with the customary coatings containing, if appropriate, opacifying agents, for example sugar, coating laquer, and can also be so composed that they release the active compound(s), if appropriate with a delay, only or preferably in a certain part of the intestinal tract, in which case, for example, polymeric substances and waxes can be used as embedding materials.

If appropriate, the active compound(s) may also be present in microencapsulated form with one or more of the abovementioned excipients.

In addition to the active compound(s), suppositories may contain the customary water-soluble or water-insoluble excipients, for example polyethylene glycols, fats, for example cocoa fat and higher esters (for example $C_{14}$-alcohol with $C_{16}$-fatty acid or mixtures of these substances).

Ointments, pastes, creams and gels may contain the customary excipients in addition to the active compound(s), for example animal and vegetable fats and their derivatives, waxes, paraffins, emulsifiers, starch, tragacanth, cellulose derivatives, polyacrylates, polyethylene glycols, silicones, bentonites, talc, silica and zinc oxide or mixtures of these substances.

Sprays and powders may contain the customary excipients in addition to the active compound(s), for example lactose, talc, silica, aluminum hydroxide, calcium silicate and polyamide powder or mixtures of these substances. Sprays may additionally contain the customary propellants, for example chlorofluorohydrocarbons.

Solutions and emulsions may contain the customary excipients, such as solvents, solubilizers and emulsifiers, for example water, ethyl alcohol, isopropyl alcohol, ethyl carbonate, ethyl acetate, benzyl alcohol, benzyl benzoate, propylene glycol, 1,3-butylene glycol, oils, in particular cottonseed oil, groundnut oil, cashew nut oil, maize germ oil, olive oil, castor oil and sesame oil, glycerol, glycerol formal, polyethylene glycols and fatty acid esters of sorbitan or mixtures of these substances in addition to the active compound(s).

For parenteral administration, the solutions and emulsions may also be present in sterile and blood-isotonic form.

Suspensions may contain the customary excipients, such as liquid diluents, for example ethyl alcohol, propylene glycol, suspending agents, for example ethoxylated isostearyl alcohols, polyoxyethylene sorbitol and sorbitan esters, microcrystalline cellulose, aluminum metahydroxide, bentonite, agar-agar or tragacanth or mixtures of these substances in addition to the active compound(s).

The said formulation forms may also contain colorants, preservatives and also odor-improving and flavor-improving additives, for example peppermint oil and eucalyptus oil and sweeteners, for example saccharin.

The therapeutically active compounds should preferably be present in the abovementioned pharmaceutical preparations in a concentration of about 0.1 to 99.5, preferably 0.5 to 95% by weight, of the total mixture.

The abovementioned pharmaceutical preparations may also contain further pharmaceutical active compounds in addition to the active compounds according to the invention.

The preparation of the abovementioned pharmaceutical preparations takes place in a customary manner by known methods, for example by mixing the active compound with the excipients.

The present invention also includes the use of the active compounds according to the invention, and also of pharmaceutical preparations which contain one or more active compound, in human and veterinary medicine for the prophylaxis, amelioration and/or cure of the abovementioned diseases.

The active compounds or the pharmaceutical preparations may be administered locally, orally, parenterally, rectally and/or as an aerosol, preferably parenterally.

In general, it has proved advantageous to administer the active compound(s) in total amounts of about 0.1 to about 100, preferably 0.5 to 50 mg/kg of body weight every 24 hours, if appropriate in the form of several individual doses, to attain the desired results.

However, it may be necessary to depart from the dosages mentioned, depending on the type and the body weight of the subject to be treated, the nature and severity of the disease, the type of preparation and the administration of the medicament and also the time period or interval within which the administration takes place. Thus in some cases it may be sufficient to manage with less than the abovementioned amount of active compound, whereas in other cases the abovementioned amount of active compound must be exceeded.

The following examples further illustrate the invention, but in no way limit its scope.

EXAMPLE 1

N,N'-1,3-propanediylbis-D-gluconamide 7.13 g of D(+)-glucono-1,5-lactone are dissolved in 40 ml of amine-free dimethylformamide and 1.67 ml of 1,3-diaminopropane are added. The mixture is then warmed to 60° C. and stirred for 5 hours. The resulting precipitate is filtered off, washed with methanol and dried. 7.96 g of a white powder are obtained.

Melting point: 165-173° C.

IR (KBr): v =3540, 2960, 2915, 2890, 1660, 1537, 1100, 1040 cm$^{-1}$ $^1$H-NMR (D$_2$O): δ1.76 (d, 2H, 6.5 Hz); 3.30 (t, 4H, 6.5 Hz); 3.4–4.0 (m, 8H); 4.09 (m, 2H); 4.30 (d, 2H, 3 Hz); 4.70 (H$_2$O, int. std.)

EXAMPLE 2

N,N'-1,12-dodecanediylbis-D-gluconamide 7.1 g of D-glucono-1,5-lactone are suspended in 90 ml of dimethylformamide, 4.0 g of 1,12-diaminododecane are added and the mixture is stirred for 5 hours at 60° C. After cooling, the mixture is stirred into 0.3 liters of methanol, and the solid is collected and washed with methanol. The solid is then suspended in 1N HCl, stirred for 1 hour at room temperature, and the solid is collected again and washed with water, acetone and finally with diethyl ether. 9.9 g of a white powder are obtained.

Melting point: 192-195° C.

IR (KBr): v=2920, 2850, 1630, 1550, 1085, 1027 cm$^{-1}$ $^1$H-NMR (DMSO-d$_6$): δ0.7–1.8 (m, 20H); 3.06 (m, 4H); 3.25-3.75 (m, 8H); 3.75-4.2 (m, 4H); 4.40 (S, 10H); 7.51 (t, 2H, 5.5 Hz); int. std.: tetramethylsilane

EXAMPLE 3

N,N'-1,3-propanediylbis-[4-O-β-D-galactopyranosyl-D-gluconamide]

395.4 g of calcium lactobionate are dissolved in 1.2 liters of water and the solution is treated for 1 hour with 0.7 liter of Lewatit S 100 (H+form) in a batch process. The mixture is filtered with suction and the exchanger is washed with 2×1 liter of water. The combined eluates are concentrated substantially in vacuo. The glass-like residue is then dissolved in 800 ml of amine-free dimethylformamide, 800 ml of n-hexane are added and the mixture is heated to boiling in a water separator with vigorous stirring. After water separation is complete, the n-hexane is distilled off, 43 ml of 1,3-diaminopropane are added and the mixture is stirred for 7 hours at 63° C. The mixture is then stirred into 5 liters of isopropanol, and the solid is collected and washed with 1 liter of isopropanol. After drying, 350 g of a white solid are obtained. For purification, this is dissolved in 2 liters of water. The solution is treated for 1 hour with 100 ml of Lewatit S 100 (H+form), then with 100 ml of Amberlyst A 21 (OH$^-$form). After freezedrying, the title compound is obtained in pure form.

Melting point: 125-132° C.

IR (KBr): v=2930, 1645, 1550, 1080 cm$^{-1}$

1H-NMR (D$_2$O): δ 1.75 (dl.2H, 6HZ); 3.27 (t, 4H, 6 Hz); 3.4–4.1 (m, 20H); 4.15 (t, 2H, 3 Hz); 4.39 (d, 2H, 3 Hz); 4.54 (d, 2H, 7 Hz); 4.70 (H$_2$O, int. std.)

$^{13}$C-NMR (D$_2$O): δ 30.79; 38.99; 63.73; 64.65; 71.30; 73.12; 73.74; 74.14; 74.50; 75.06; 75.18; 77.99; 83.71; 106.10; 176.84 int. std.: CH30H δ 51.56

EXAMPLE 4

N,N'-1,6-hexanediylbis-[4-O-β-D-galactopyranosyl-D-gluconamide]

17.0 g of lactobiono-1,5-lactone are suspended in 100 ml of amine-free dimethylformamide, 2.9 g of 1,6-diaminohexane are added and the mixture is stirred for 6 hours at 80° C. After cooling, the mixture is filtered and the filtrate is stirred into 1 liter of diethyl ether. The partly oily precipitate is dissolved in 50 ml of water and treated with 80 ml of ion exchanger (Merck 4765, H$^+$ form). The mixture is filtered and, after lyophilization, 19.5 g of colorless powder which decomposes from 175° C. with brown coloration are obtained.

IR: v=2930, 2860, 1645, 1548, 1080 cm$^{-1}$ $^1$H-NMR (D$_2$O): δ 1.0–1.8 (m, 8H); 3.25 (t, 4H, 5.5 Hz); 3.3–4.1 (m, 20H); 4.15 (t, 2H, 3 Hz); 4.38 (d, 2H, 3 Hz); 4.55 (d, 2H, 7 Hz); 4.70 (H$_2$O) int. std.: 3-trimethylsilylpropanesulfonic acid Na salt $^{13}$C-NMR (D$_2$O): 28.19; 30.89; 41.63; 63.68; 64.64; 71.25; 73.06; 73.72; 74.12; 74.96; 75.18; 77.97; 83.61; 106.08; 176.42 int. std.: CH$_3$OH δ 51.54

EXAMPLE 5

N,N'-1,12-Dodecanediylbis-[4-O-β-D-galactopyranosyl-D-gluconamide]

40.8 g of lactobiono-1,5-lactone are suspended in 150 ml of amine-free dimethylformamide, 12.0 g of 1,12-diaminododecane are added and the mixture is stirred for 6 hours at 60° C. The mixture is added dropwise with stirring to 1.5 liters of isopropanol. The precipitate is washed with isopropanol and dissolved in 250 ml of water. The solution is treated first with 20 ml of an acid ion exchanger (Lewatit S 100), then with a basic ion exchanger (Merck 4767). After lyophilization, 35.0 g of a colorless powder are obtained.

Melting point: 79-81° C.

IR: v=2920, 2850, 1645, 1550, 1080 cm$^{-1}$ $^1$H-NMR (D$_2$O): δ 0.8–1.9 (m, 20H); 3.24 (t, 4H, 5.5 Hz); 3.4–4.1 (m, 20H); 4.17 (t, 2H, 3 Hz); 4.38 (d, 2H, 3 Hz); 4.55 (d, 2H, 7 Hz); 4.68 (H$_2$O, int. std.)

$^{13}$C-NMR (D$_2$O): δ 29.02; 31.36; 31.70; 41.86; 63.64; 64.69; 71.20; 73.08; 73.72; 74.17; 75.03; 75,20; 77.97; 83.72; 106.12; 176.24; int. std. CH30H δ 51.56

Example 6

N,N'-1,9-Nonanediylbis-[4-O-β-D-galactopyranosyl-D-gluconamide]

Preparation and purification are analogous to Example 5. 15.0 g of the title compound are obtained from 15.0 g of lactobiono-1,5-lactone and 3.47 g of 1,9-diaminononane.

IR: v=2930, 2860, 1660, 1545, 1080 cm$^{-1}$ $^1$H-NMR (D$_2$O) δ 0.9–1.8 (m, 14H); 3.20 (t, 4H, 5.5 Hz); 3.3–4.1 (m, 20H); 4.15 (t, 2H, 3 Hz); 4.38 (d, 2H, 3 Hz); 4.55 (d, 7 Hz); 4.68 (H$_2$O, int. std.)

EXAMPLE 7

N,N'-1,12-Dodecanediylbis-(4-0-β-D-glucopyranosyl-D-gluconamide)

2.04 g of cellobiono-1,5-lactone (H. W. Diehl et al., Carbohydr. Res. 38, 364 (1974)) are reacted with 0.60 g of 1,12-diaminododecane analogously to Example 5 and 0.60 g of the title compound are obtained.

IR: $v=2925, 2850, 1645, 1545, 1075, 1040$ cm$^{-1}$ $^1$H-NMR (D$_2$O): δ 0.7–1.9 (m, 20H); 3.0–4.6 (m, 30H); 4.68 (H$_2$O int. std.)

EXAMPLE 8

N,N'-1,12-Dodecanediylbis-(4-0-α-D-glucopyranosyl-D-gluconamide) 20.0 g of calcium maltobionate (W. N. Emmerling, B. Pfannemüller, Starch 33, 202, (1981)) are reacted with 1,12-diaminododecane analogously to Example 3 and 17.8 g of product are obtained.

IR: $v=2925, 2850, 1650, 1545, 1145, 1075, 1030$ cm$^{-1}$ $^1$H-NMR (D$_2$O): δ 0.7–1.9 (m, 20H); 3.20 (t, 4H, 5.5 Hz); 3.3–4.4 (m, 24H); 5.15 (d, 2H, 3 Hz); 4.68 (H$_2$O, int. std)

EXAMPLE 9

N,N'-1,12-Dodecanediylbis-(6-O-α-D-galactopyranosyl)-D-gluconamide)

3.96 g of potassium melibionate (Sigma Chemie) are reacted with 1.00 g of 1,12-diaminododecane analogously to Example 3 and 3.3 g of the title compound are obtained.

Melting point: 114–123° C.

IR (KBr): $v=2925, 1855, 1645, 1550, 1150, 1080, 1030, 980$ cm$^{-1}$ $^1$H-NMR (D$_2$O): δ 0.8–1.8 (m, 20H); 3.20 (m, 4H); 3.4–4.2 (m, 22H), 4.29 (d, 2H, 3 Hz); 4.95 (s, 2H); 4.68 (H$_2$O, int. std.)

EXAMPLE 10

N,N'-1,3-Propanediylbis-(6-O-α-D-galactopyranosyl-D-gluconamide)

Preparation is analogous to Example 9. 3.0 g of product are obtained from 3.96 g of potassium melibionate and 0.37 g of 1,3-diaminopropane.

Melting point: 90–96° C.

IR (KBr): $v=2925, 1645, 1550, 1152, 1080, 1030, 975$ cm$^{-1}$ $^1$H-NMR (D$_2$O): δ 1.76 (dt, 2H, 6.5 Hz); 3.30 (t, 4H, 6.5 Hz); 3.4–4.2 (m, 22H); 4.33 (d, 2H, 3 Hz); 4.96 (s, 2H); 4.70 (H$_2$O, int. std.)

$^{13}$C-NMR (D$_2$O): δ 30.73; 38.96; 63.75; 70.94; 74.13; 71.90; 72.12; 73.06; 73.52; 74.52; 75.97; 100.99; 176.91

EXAMPLE 11

N,N'-α-α'-m-Xylenediylbis-[4–0-β-D-galactopyranosyl-D-gluconamide]

If 17.0 g of lactobiono-1,5-lactone and 3.3 ml of 3-(aminomethyl)benzylamine are used in a process according to Example 5, then 12.2 g of the title compound are obtained in the same way as colorless powder.

IR: $v=2920, 1665, 1545, 1080$ cm$^{-1}$ $^1$H-NMR (D$_2$O): δ 3.3–4.6 (m, 30H); 4.68 (H$_2$O); 7.24 (m, 4H)

EXAMPLE 12

N,N'-4,4'-Dicyclohexylmethanediylbis-[4-O-β-D-galactopyranosyl-D-gluconamide]

Preparation and purification from 17.0 g of lactobiono-1,5-lactone and 5.3 g of 4,4'-diaminodicyclohexylmethane are analogous to Example 5.

Yield: 21.3 g.

IR: $v=2930, 2850, 1645, 1545, 1080$ cm$^{-1}$ $^1$H-NMR (D$_2$O): δ 0.6–2.2 (m, 20H); 3.2–4.6 (m, 28H) 4.68 (H$_2$O)

EXAMPLE 13

N,N'-1,6-(3,4-Dithiahexanediylbis)-4-O-β-D-galactopyranosyl-D-gluconamide 6.9 ml of triethylamine are added at room temperature to 17.0 g of lactobiono-1,5-lactone and 5.63 g of cystamine dihydrochloride in 50 ml of amine-free DMF and the mixture is subsequently stirred for 6 hours at 60° C. It is then precipitated using 500 ml of ethanol and the precipitate is further treated as in Example 5. 13.2 g of white powder are obtained.

IR $v=2925, 1650, 1545, 1080$ cm$^{-1}$ $^1$H-NMR (D$_2$O): δ 2.90 (t, 4H, 6 Hz); 3.2–4.1 (m, 24H); 4.16 (t, 2H, 3 Hz); 4.38 (d, 2H, 3 Hz); 4.55 (d, 2H, 7 Hz); 4.68 (H$_2$O, int. std.)

EXAMPLE 14

N,N'-1,7-(4-Azaheptanediylbis)-4-O-β-D-galactopyranosyl-D-gluconamide 17.0 g of lactobiono-1,5-lactone are suspended in 100 ml of amine-free dimethylformamide, 2.28 ml of bis-(3-aminopropyl)amine are added at room temperature and the mixture is stirred for 10 hours. It is then stirred for 4 hours at 40° C. and filtered. The filtrate is stirred into 900 ml of acetone and 23.0 g of white crystals are obtained after washing with acetone and drying. These are dissolved in 80 ml of water and precipitated using 900 ml of acetone. The partly oily precipitate is dissolved in 150 ml of water, filtered and lyophilized. Yield: 16.5 g.

IR: $v=2920, 1650, 1545, 1080$ cm$^{-1}$ $^1$H-NMR (D$_2$O): 1.82 (dt.4H, 6 Hz); 2.91 (t, 4H, 6 Hz); 3.30 (t, 4H, 6 Hz); 3.45–4.6 (m, 26H); 4.68 (H$_2$O)

Example 15

N,N'-1,12-(4,9-Dioxadodecanediylbis)-4-O-β-D-galactopyranosyl-D-gluconamide

Preparation and purification are analogous to Example 5. 18.9 g of the title compound are obtained from 17.0 g of lactobiono-1,5-lactone and 5.1 g of 1,12-diamino-b 4,9-dioxadodecane.

$^1$H-NMR (D$_2$O) δ 1.4–2.0 (m, 8H); 3.1–4.1 (m, 32H); 4.6 (t, 2H, 3 Hz); 4.38 (d, 2H, 3 Hz); 4.55 (d, 2H, 7 Hz)

EXAMPLE 16

N,N'-Dimethyl-N,N'-1,2-ethanediylbis-(4-O-β-D-galactopyranosyl-D-gluconamide)

Preparation and purification are analogous to Example 5. 3.0 g of the title compound are obtained from 3.40 g of lactobiono-1,5-lactone and 0.44 g of N,N'-dimethylethylenediamine.

Melting point: 125–133° C.

IR (KBr): $v=2930, 1640, 1400, 1075$ cm$^{-1}$ $^1$H-NMR (D$_2$O): δ2.99, 3.16 (2S, 6H); 3.3–4.3 (m, 28H); 4.49 (d, 2H, 7 Hz); 4.68 (H$_2$O, int. std.)

EXAMPLE 17

N,N'-1,5-(1-Ethoxycarbonyl)pentanediylbis-(4-O-β-D-galactopyranosyl-D-gluconamide)

2.47 g of lysine ethyl ester dihydrochloride are suspended in 40 ml of amine-free dimethylformamide, 3.0 ml of triethylamine are added and the mixture is stirred for 15 minutes. 6.8 g of lactobiono-1,5-lactone are then added, and the mixture is heated to 60° C. and stirred for 1 day. It is then filtered and the filtrate is stirred into 400 ml of isopropanol. The precipitate is collected, dissolved in 60 ml of dimethylformamide and precipitated again using 300 ml of isopropanol. The precipitation is repeated, the precipitate is washed with isopropanol and diethyl ether and 4.05 g of a white powder are thus obtained.

Melting point: 106° C.

IR: $v=2930, 1735, 1655, 1550, 1075$ cm$^{-1}$ $^1$H-NMR (D$_2$O): δ 1.25 (t, 3H, 7 Hz); 1.2–2.2 (m, 6H); 3.25 (t, 2H, 5.5 Hz); 3.4–4.6 (m, 29H); 4.68 (H$_2$O, int. std.)

EXAMPLE 18

Decasodium
N,N'-1,3-propanediylbis-(2,3,4,5,6-penta-O-sulfo-D-gluconamide)

4.30 g of N,N'-1,3-propanediylbis-D-gluconamide are suspended in 50 ml of dry dimethylformamide and heated to 40° C., and 23.9 g of pyridine-sulfur trioxide complex are added with stirring. After a few minutes, the product precipitates out in the form of the pyridinium salt as an oil. After 1 hour, the mixture is allowed to cool and the supernatant solution is decanted off. The oil is dissolved in 50 ml of water and brought to pH=10 using 6N sodium hydroxide solution. The solution is made up to 90 ml using water and stirred into 350 ml of a 1% strength sodium acetate solution. The precipitate is washed with methanol and dried. 18.6 g of a colorless powder are obtained. This is dissolved in 186 ml of water. 227 ml of methanol are stirred into the solution and it is allowed to stand for 15 hours. The supernatant is decanted from the deposited oil and the latter is triturated with methanol. The precipitation is repeated until the title compound is pure.

Decomposition from 190° C. with brown coloration.

IR (KBr): $v=2960, 1670, 1555, 1250, 1073, 1045, 1019, 770$ cm$^{-1}$ $^1$H-NMR (D$_2$O): δ 1.87 (dt, 2H, 7 Hz); 3.36 (dt, 4H, 7 Hz); 3.9–4.6 (m, 4H); 4.8–5.4 (m, 8H); 4.68 (H$_2$O, int. std.) $[α]_{20}^D = +26.2$ (c =5 in H$_2$O)

Elemental analysis: calc.: N 22.10% S 1.93%; found: N 22.29% S 1.83%.

$^{13}$C-NMR (D$_2$O): 29.97; 39.69; 69.06; 77.68; 78.10; 78.39; 79.65; 171.33; int. std.: CH$_3$OH δ 51.56

EXAMPLE 19

Decasodium
N,N'-1,12-dodecanediylbis-(2,3,4,5,6-penta-D-sulfo-D-gluconamide)

5.60 g of N,N'-1,12-dodecanediylbis-D-gluconamide are reacted with 25.5 g of pyridine-sulfur trioxide complex analogously to Example 18 and 20.5 g of crude product are obtained. The pure product is obtained by gel chromatography of an aqueous solution on a Sephadex G 25 column. After freeze-drying, a colorless powder which decomposes between 175° C. and 189° C. with brown coloration is obtained.

IR (KBr): $v=2930, 2855, 1665, 1555, 1250, 1072, 1042, 1010$ cm$^{-1}$ $^1$H-NMR (D$_2$O): δ 1.0–1.9 (m, 20H); 3.32 (m, 4H); 4.2–4.6 (m, 4H); 4.9–5.3 (m, 8H); 4.68 (H$_2$O, int. std.)

$^{13}$C-NMR (D$_2$O): δ 28.72; 30.52; 31.02; 42.30; 69.22; 77.67; 78.34; 78.65; 79.91; 171.09; int. std. CH$_3$OH δ 51.56

EXAMPLE 20

Hexadecasodium
N,N'-1,3-propanediylbis-[2,3,5,6-tetra-O-sulfo-4-O-(2,3,4,6-tetra-O-sulfo-β-D-galactopyranosyl)-D-gluconamide]

79.1 g of calcium lactobionate are dissolved in 240 ml of water and the solution is treated with 240 ml of Lewatit S 100 (H+ form). The ion exchanger is washed using 3×200 ml of water and the combined solutions are concentrated as far as possible. The glass-like residue is dissolved in 700 ml of amine-free dimethylformamide and heated to boiling with 600 ml of n-hexane in a water separator. After water separation is complete, the n-hexane is evaporated off and 7.7 g of 1,3-diaminopropane in 50 ml of dimethylformamide are added to the solution at room temperature. After stirring for 5 hours at 60° C., the mixture is allowed to cool to about 30° C. and diluted with 450 ml of dimethylformamide, and 400 g of pyridine-sulfur trioxide complex are added rapidly in portions with stirring. The mixture is stirred for 1 hour between 40° and 45° C. and allowed to cool. The supernatant is decanted off from the deposited oil, and this is dissolved in 500 ml of water and the solution is adjusted to pH=10 using 30% strength sodium hydroxide solution. The solution is made up with water to a volume of 1.5 liters and stirred into 4.5 liters of a 1% strength methanolic sodium acetate solution. The precipitate is stirred with 1 liters of methanol, filtered off with suction and dried. 250 g of a yellowish powder are obtained. This is dissolved in 2 liters of water, 250 ml of 30% strength hydrogen peroxide are added and the mixture is stirred for 1 hour at 45° C. After cooling, it is neutralized and made up to 2.5 liters using water. The solution is stirred into 3.06 liters of methanol and allowed to stand for 15 hours. The supernatant is decanted off from deposited oil and the latter is triturated with methanol. After drying, 188.5 g of colorless powder are obtained. The precipitation procedure is repeated four times and about 50 g of the pure title compound are finally obtained as a colorless powder which turns brown from 172° C. with decomposition and does not melt under 250° C.

IR (KBr): $v=2965, 1665, 1552, 1250, 1055, 1020, 927, 820$ cm$^{-1}$ $^1$H-NMR (D$_2$O): δ 1.82 (t, 2H, 6.5 Hz); 3.35 (t, 4H, 6.5 Hz); 3.9–4.4 (m, 8H); 4.4–4.8 (m, +H$_2$O signal at 4.68 as int. std.); 4.8–5.4 (m, 10H)

$^{13}$C-NMR (D$_2$O): δ 30.31; 39.77; 68.36; 68.92; 74.22; 77.49; 77.79; 78.39; 78.76; 80.15; 103.55; 171.76; int. std.: CH$_3$OH δ 51.56

$[α]_{20}^D = +13.3°$ (c=5 in H$_2$O)

Elemental analysis: calc.: N: 1.17%) S: 21.49%; found: N: 1.16% S: 21.61%.

Example 21

Pentadecasodium
pentadeca-O-sulfo-N,N'-1,3propanediylbis(4-O-β-D-galactopyranosyl-D-gluconamide)

3.77 g of N,N'-1,3-propanediylbis(4-O-β-D-galactopyranosyl-D-gluconamide) are dissolved in 60 ml of dry dimethylformamide and 13.5 g of pyridine-sulfur trioxide complex are added in portions at 40° C. with stirring. After 1 hour, the mixture is worked up as in Example 18 and 10.3 g of yellowish, sulfate-containing crude product are obtained. This is dissolved in 90 ml of water, 10 ml of 30% strength hydrogen peroxide are added and the mixture is stirred for 1 hour at 45° C. After cooling, 230 ml of methanol are stirred in and the mixture is allowed to stand for 15 hours. The supernatant is decanted off from the deposited oil, the latter is triturated using methanol and 6.72 g of sulfate-free product (having a sulfur content of 20.6%) are obtained. This is dissolved in 67 ml of water, 82 ml of methanol are stirred in and the mixture is allowed to stand for 15 hours. The supernatant is decanted off from the deposited oil and a further 74 ml of methanol are stirred in. After 15 hours, the oil is isolated and the fractional crystallization is repeated with it several times as above until the title compound is pure. 0.53 g of colorless powder which decomposes from 180° C. with brown coloration are obtained.

IR (KBr): $v=2960$, 1660, 1550, 1250, 1055, 1020, 930, 820 cm$^{-1}$ $^1$H-NMR (D$_2$O): δ 1.87 (t, 2H, 6 Hz); 3.42 (t, 4H, 6Hz); 3.9–4.5 (m, 8H); 4.5–4.85 (m+ H$_2$O signal at 4.68 as int. std.); 4.85–5.3 (m, 10H)

$^{13}$C-NMR (D$_2$O): 30.53; 39.79; 68.46; 69.11; 72.28; 74.36; 74.56; 77.43; 77.88; 78.14; 78.49; 79.03; 79.61; 79.84; 80.43; 103.45; 171.82; 172.61; int. std.: CH$_3$OH δ 51.56

Elemental analysis: calc.: N 1.23%; S 21.04%; found: N 1.21%; S 20.91%.

EXAMPLE 22

Hexadecamorpholinium
N,N'-1,3-propanediylbis-[2,3,5,6-tetra-O-sulfo-4-O-(2,3,4,6-tetra-O-sulfo-β-D-galactopyranosyl)-D-gluconamide]

A solution of 1.76 g of the sodium salt from Example 20 is treated for 15 minutes with 16 ml of Lewatit S-100 (H+ form), the ion exchanger is filtered off and 1.03 g of morpholine are added to the filtrate. After lyophilization, 2.40 g of yellowish powder are obtained. Decomposition from 120° C. and black coloration at 210° C.

IR (KBr): $v=2950$, 2780, 1665, 1563, 1450, 1426, 1250, 1097, 1015, 925, 893, 868, 810 cm$^{-1}$ $^1$H-NMR (D$_2$O): δ 1.82 (dt, 2H; 6.5 Hz); 3.15 (m, 64H); 3.35 (m, 4H); 3.90 (m, 64H); 4.0–4.4 (m, 8H); 4.4–4.8 (m, +H$_2$O signal at 4.70 as int. std.); 4.8–5.4 (m, 10H)

EXAMPLE 23

Hexadecasodium
N,N'-1,6-hexanediylbis-[2,3,5,6-tetra-O-sulfo-4-O-(2,3,4,6-tetra-O-sulfo-β-D-galactopyranosyl)-D-gluconamide]

16.3 g of N,N'-1,6-hexanediylbis(4-O-β-D-galactopyranosyl-D-gluconamide) are reacted with 75.0 g of pyridine-sulfur trioxide complex analogously to Example 18. After the first precipitation, 56.9 g of a yellowish powder are obtained which is purified as in Example 20. About 15 g of the pure title compound are finally obtained in the form of a colorless powder which sinters from 120° C.

Decomposition from 170° C. with brown coloration.

IR (KBr): $v=2930$, 2860, 1655, 1550, 1250, 1055, 1020, 928, 810 cm$^{-1}$ $^1$H-NMR (D$_2$O): δ 1.1–1.9 (m, 8H); 3.37 (m, 4H); 3.9–4.5 (m, 8H); 4.5–4.85 (m + H$_2$O signal at 4.68 as int. std.); 4.85–5.3 (m, 10H)

$^{13}$C-NMR (D$_2$O): δ 28.42; 30.74; 42.17; 68.56; 69.01; 74.39; 77.20; 77.80; 78.37; 78.94; 80.47; 103.21; 171.27; int. std. CH$_3$OH δ 51.56

$[\alpha]_{20}^D = +9.9$ (c=5 in H$_2$O)

EXAMPLE 24

Hexadecasodium
N,N'-1,9-nonanediylbis-[2,3,5,6-tetra-O-sulfo-4-O-(2,3,4,6-tetra-O-sulfo-β-D-galactopyranosyl)-D-gluconamide]

Preparation and purification are analogous to Example 23. 45.0 g of crude product are obtained from 15.0 g of N,N'-1,9-nonanediylbis(4-O-β-D-galactopyranosyl-D-gluconamide) and 63.0 g of pyridine-sulfur trioxide complex. After purification: 10.5 g of colorless powder.

Decomposition between 192–210° C. with brown coloration

IR (KBr): $v=2935$, 2860, 1665, 1555, 1250, 1057, 1020, 925, 815 cm$^{-1}$ $^1$H-NMR (D$_2$O): δ 0.9–1.9 (m, 14H); 3.29 (t, 4H, 6.5 Hz); 3.8–4.45 (m, 8H); 4.45–4.8 (m+H$_2$O signal at 4.68 as int. std.); 4.8–5.4 (m, 10H)

$^{13}$C-NMR (D$_2$O): 4 28.77; 30.83; 31.09; 31.32; 42.19; 68.69; 68.99; 74.46; 77.12; 77.79; 78.33; 78.93; 80.51; 103.11; 121.21 int. std.; CH$_3$OH, δ 51.56

EXAMPLE 25

Hexadecasodium
N,N'-1,12-dodecanediylbis-[2,3,5,6-tetra-O-sulfo-4-O-(2,3,4,6-tetra-O-sulfo-β-D-galactopyranosyl)-D-gluconamide]

Preparation and purification are analogous to Example 23. 13.30 g of crude product are obtained from 4.23 g of N,N'-1,12-dodecanediylbis (4-O-β-D-galactopyranosyl-D-gluconamide) and 19.1 g of pyridine-sulfur trioxide complex. After purification: 3.5 g of pure title compound are obtained as colorless powder.

Decomposition between 188–198° C. with brown coloration

IR (KBr): $v=2940$, 2880, 1665, 1555, 1250, 1055, 1020, 930, 820 cm$^{-1}$ $^1$H-NMR (D$_2$O): δ 0.9–1.9 (m, 20H); 3.35 (t, 4H, 6.5 Hz); 3.9–4.5 (m, 8H); 4.5–4.8 (m, +H$_2$O signal at 4.70 as int. std.); 4.8–5.4 (m, 10H)

$^{13}$C-NMR (D$_2$O): δ 28.74; 30.80; 31.09; 31.44; 42.18; 68.76; 68.96; 74.50; 77.08; 77.80; 78.29; 78.94; 80.51; 103.07; 171.19 int. std.; CH$_3$OH δ 51.56

EXAMPLE 26

Hexadecasodium
N,N'-1,12-dodecanediylbis-[2,3,5,6-tetra-sulfo-4-O-(2,3,4,6-tetra-O-sulfo-β-D-glucopyranosyl)-D-gluconamide]

0.68 g of crude or 0.10 g of pure product are obtained from 0.34 g of N,N'-1,12-dodecanediylbis(4-O-β-D- glucopyranosyl-D-gluconamide) and 1.12 g of pyridine-sulfur trioxide complex analogously to Example 23.

Decomposition from 148° C. to 159° C. with brown coloration.

IR (KBr): v=2930, 2855, 1670, 1560, 1250, 1070, 995, 935, 800 cm$^{-1}$ $^1$H-NMR (D$_2$O): δ 0.8–1.8 (m, 20H); 3.30 (m, 4H); 3.7–4.8 (m +H$_2$O signal at 4.68 as int. std.); 4.8–5.3 (m, 10H)

$^{13}$C-NMR (D$_2$O): δ 28.92; 30.95; 31.32; 31.64; 42.34; 69.20; 70.12; 75.57; 77.44; 77.67; 77.85; 79.33; 79.41; 79.97; 81.08; 102.53; 171.27; int. std.: CH$_3$OH δ 51.56

EXAMPLE 27

Hexadecasodium
N,N'-1,12-dodecanediylbis-[2,3,5,6-tetra-sulfo-4-O-(2,3,4,6-tetra-O-sulfo-α-D-glucopyranosyl)-D-gluconamide]

47.5 g of crude or 3.0 g of pure product are obtained from 12.8 g of N,N'-1,12-dodecanediylbis(4-O-α-D-glucopyranosyl-D-gluconamide) and 64.6 g of pyridine-sulfur trioxide complex analogously to Example 23.

Decomposition from 175° C. to 189° C. with brown coloration.

IR (KBr): v=2930, 2860, 1660, 1560, 1250, 1000, 943, 805 cm$^{-1}$ $^1$H-NMR (D$_2$O): δ 1.0–1.9 (m, 20H); 3.27 (m, 4H); 4.0–4.82 (m +signal for H$_2$O at 4.68 as int. std.); 4.82–5.25 (m, 10H); 5.52 (d, 2H, 3 Hz)

$^{13}$C-NMR (D$_2$O): δ 28.84; 30.69; 31.15; 31.47; 42.41; 68.51; 69.29; 71.95; 76.14; 76.82; 77.91; 78.30; 78.44; 79.98; 98.93; 171.27

EXAMPLE 28

Hexadecasodium
N,N'-1,12-dodecanediylbis-[2,3,4,5-tetra-sulfo-6-O-(2,3,4,6-tetra-O-sulfo-α-D-galactopyranosyl)-D-gluconamide]

9.7 g of crude or 3.4 g of pure product, which sinters at 57° C., are obtained analogously to Example 23 from 3.30 g of N,N'-1,12-dodecanediylbis(6-O-α-D-galactopyranosyl-D-gluconamide) and 14.9 g of pyridine-sulfur trioxide complex.

Decomposition from 182° C. with brown coloration.

IR (KBr): v=2930, 2855, 1650, 1555, 1250, 1050, 1027, 830 cm$^{-1}$ $^1$H-NMR (D$_2$O): δ 1.0–1.9 (m, 20H); 3.25 (m, 4H); 3.9–4.4 (m, 8H); 4.4–4.8 (m+H$_2$O signal at 4.68 as int. std.); 4.8–5.25 (m, 10H); 5.38 (d, 2H, 3 Hz)

$^{13}$C-NMR (D$_2$O): δ 28.72; 30.58; 31.03; 31.34; 42.30; 69.14; 69.77; 70.66; 74.51; 74.92; 77.91; 78.21; 78.49; 78.93; 80.75; 99.12; 171.26; int. std.: CH$_3$OH δ 51.56

EXAMPLE 29

Hexadecasodium
N,N'-1,3-propanediylbis-[2,3,4,5-tetra-O-sulfo-6-O-(2,3,4,6-tetra-O-sulfo-α-D-galactopyranosyl)-D-gluconamide]

0.96 g of crude or 0.50 g of pure product are obtained from 0.34 g of N,N'-1,3-propanediylbis(6-O-α-D-galactopyranosyl-D-gluconamide) and 2.0 g of pyridinesulfur trioxide complex analogously to Example 23. Decomposition from 168° C. with brown coloration IR (KBr): v=1640, 1550, 1250, 1050, 1025, 830 cm$^{-1}$ $^1$H-NMR (D$_2$O): δ 1.85 (t, 2H, 6.5 Hz); 3.35 (t, 4H, 6.5 Hz); 3.9–4.4 (m, 8H); 4.4–4.8 (m+H$_2$O signal at 4.68 as int. std.); 4.8–5.25 (m, 10H); 5.36 (d, 2H, 3 Hz)

$^{13}$C-NMR (D$_2$O): δ 30.13; 39.84; 69.17; 69.86; 70.74; 74.53; 74.97; 78.00; 78.17; 78.37; 79.00; 80.81; 99.18; 171.70; int. std.: CH$_3$OH δ 51.57

EXAMPLE 30

Hexadecasodium
N,N'-α,α'-m-xylenediylbis-[2,3,5,6-tetra-O-sulfo-4-O-(2,3,4,6-tetra-O-sulfo-β-D-galactopyranosyl)-D-gluconamide]

28.0 g of crude or 5.3 g of pure product are obtained from 12.0 g of N,N'-α,α'-m-xylenediylbis(4-O-β-D-galactopyranosyl-D-gluconamide) and 58.8 g of pyridine-sulfur trioxide complex analogously to Example 23.

Decomposition from 157° C. with brown coloration.

IR (KBr): v=2960, 1660, 1550, 1250, 1055, 1020, 930, 815 cm$^{-1}$ $^1$H-NMR (D$_2$O): δ 3.9–4.85 (m+H$_2$O signal at 4.68 as int. std.), 4.85–5.4 (m, 10H); 7.38 ; (s, 4H)

$^{13}$C-NMR (D$_2$O): δ 45.51; 68.63; 69.15; 74.42; 77.24; 77.67; 77.91; 78.49; 79.08; 80.70; 103.29; 128.15; 128.86; 131.64; 140.80; 171.88; int. std. CH$_3$OH δ 51.56

EXAMPLE 31

Hexadecasodium
N,N'-4,4-dicylcohexylmethanediylbis-[2,3,5,6-tetra-O-sulfo-4-O-(2,3,4,6-tetra-O-sulfo-β-D-galactopyranosyl)-D-gluconamide]

70.7 g of crude or 15.2 g of pure product, which sinters from 120° C., are obtained analogously to Example 23 from 25.7 g of N,N'-4,4'-dicyclohexylmethanediylbis(4-O-β-D-galactopyranosyl-D-gluconamide) and 114.7 g of pyridine-sulfur trioxide complex.

Decomposition from 180° C. with brown coloration.

IR (KBr): v=290, 2860, 1660, 1550, 1250, 1055, 1020, 928, 815 cm$^{-1}$ $^1$H-NMR (D$_2$O): δ 0.6–2.4 (m, 20H); 3.65 (m, 2H); 3.9–4.5 (m, 8H); 4.5–4.85 (m+H$_2$O signal at 4.68 as int. std.); 4.85–4 (m, 10H)

$^{13}$C-NMR (D$_2$O): δ 30.18; 30.36; 30.75; 34.09; 44.40; 46.20; 49.45; 52.33; 68.27; 68.75; 74.35; 77.80; 78.41; 78.68; 79.49; 104.09; 170.61; int. std. CH$_3$OH δ 51.56 [α]$_{20}^D$=+10.0 (c=5 in H$_2$O)

EXAMPLE 32

Hexadecasodium
N,N'-1,6-(3,4-dithiahexanediylbis)[2,3,5,6-tetra-O-sulfo-4-O-(2,3,4,6-tetra-O-sulfo-β-D-galactopyranosyl)-D-gluconamide]38.0 g of crude and 8.5 g of pure product are obtained from 11.2 g of
N,N'-1,6-(3,4-dithiahexanediylbis)4-O-β-D-galactopyranosyl-D-gluconamide and 53.4 g of
pyridine-sulphur trioxide complex analogously to Example 23.

Decomposition from 163° C. with brown coloration.

IR (KBr): v=2965, 1665, 1550, 1250, 1055, 1015, 930, 810 cm$^{-1}$ $^1$H-NMR (D$_2$O): δ 2.96 (t, 4H, 6.5 Hz); 3.69 (m, 4H); 4.0–4.47 (m, 8H); 4.45–4.8 (m+H$_2$O signal at 4.68 as int. std.); 4.8–5.3 (m, 10H)

$^{13}$C-NMR (D$_2$O): δ 38.72; 41.06; 68.68; 69.05; 74.48; 77.40; 77.87; 78.46; 80.46; 103.48; 171.86; int. std. CH$_3$OH δ 51.56

EXAMPLE 33

Hexadecasodium N,N'-1,7-(4-azaheptanediylbis)[2,3,5,6-tetra-O-sulfo-4-O-(2,3,4,6-tetra-O-sulfo-β-D-galactopyranosyl)-D-gluconamide]

15.4 g of crude and 2.2 g of pure product are obtained from 11.0 g of N,N'-1,7-(4-azaheptanediylbis)-O-β-D-galactopyranosyl-D-gluconamide and 50.0 g of pyridine-sulfur trioxide complex analogously to Example 23.

Decomposition from 165° C. with brown coloration.

IR (KBr): ν=2960, 2925, 2855, 1650, 1550, 1250, 1055, 1020, 927, 820 cm$^{-1}$ $^1$H-NMR (D$_2$O): δ 2.98 (m, 2H); 3.17 (t, 4H, 7 Hz); 3.44 (t, 4H, 6 Hz); 3.9–4.4 (m, 8H); 4.4–4.85 (m+H$_2$O signal as int. std. at 4.68); 4.85–5.3 (m, 10H)

$^{13}$C-NMR (D$_2$O): δ 28.11; 39.08; 48.12; 68.65; 69.24; 74.45; 76.94; 77.93; 78.46; 79.09; 80.71; 103.13; 172.06

EXAMPLE 34

Hexadecasodium N,N'-1,12-(4,9-dioxadodecanediylbis)[2,3,5,6-tetra-O-sulfo-4-O-(2,3,4,6-tetra-O-sulfo-β-D-galactopyranosyl)-D-gluconamide]

37.1 g of crude and 9.3 g of pure product, which sinters from 120° C., are obtained from 18.2 g of N,N'-1,12-(4,9-dioxadodecanediylbis)4-O-β-D-galactopyranosyl-D-gluconamide and 59.0 g of pyridine-sulfur trioxide complex according to Example 23.

Decomposition from 170° C. with brown coloration.

IR (KBr): ν=2960, 2880, 1665, 1555, 1250, 1055, 1022, 928, 815 cm$^{-1}$ $^1$H-NMR (D$_2$O): δ 1.64 (m, 4H); 1.88 (t, 4H, 6.5 Hz); 3.0–3.9 (m, 12H); 3.9–4.45 (m, 8H); 4.45–4.8 (m+H$_2$O signal at 4.68 as int. std.); 4.8–5.3 (m, 10H)
13

$^{13}$C-NMR (D$_2$O): δ 27.82; 30.78, 39.02; 68.64; 69.01; 70.54; 72.96; 74.44; 77.02; 77.79; 78.33; 78.94; 80.52; 103.10; 171.45; int. std.: CH$_3$OH δ 51.56

[α]$_{20}^D$= +9.0 (c=5 in H$_2$O)

EXAMPLE 35

Hexadecasodium N,N'-dimethyl-N,N'-1,2-ethanediylbis-[2,3,5,6-tetra-O-sulfo-4-O-(2,3,4,6-tetra-O-sulfo-β-D-galactopyranosyl)-D-gluconamide]

8.2 g of crude and 1.2 g of pure product are obtained from 2.50 g of N,N'-dimethyl-N,N'-1,2-ethanediylbis-(4-O-β-D-galactopyranosyl-D-gluconamide) and 12.4 g of pyridine-sulfur trioxide complex analogously to Example 23.

Decomposition from 188°–200° C. with brown coloration.

IR (KBr): ν=2970, 1650, 1250, 1015, 930, 815 cm$^{-1}$ $^1$H-NMR (D$_2$O): δ 3.0–4.0 (m with s at 3.35; 10H); 4.0–4.7 (m, 14H); 4.70 (H$_2$O, int. std.); 4.9–5.4 (m, 10H); 5.54 (d, 2H, 4 Hz)

$^{13}$C-NMR (D$_2$O): δ 38.96; 48.25; 68.36; 69.25; 74.17; 75.11; 77.26; 77.73; 78.00; 78.45; 78.76; 79.80; 103.35; 171.25; int. std.: CH$_3$OH, δ 51.56

EXAMPLE 36

Hexadecasodium N,N'-1,5-(1-ethoxycarbonyl)pentanediylbis-[2,3,5,6-tetra-O-sulfo-4-O-(2,3,4,6-tetra-O-sulfo-β-D-galactopyranosyl)-D-gluconamide]

8.7 g of crude and 1.2 g of pure product, which sinters from 60° C., are obtained from 3.6 g of N,N'-1,5-(1-ethoxycarbonyl)pentanediylbis(4-O-β-D-galactopyranosyl-D-gluconamide) and 15.8 g of pyridine-sulfur trioxide complex according to Example 23.

Decomposition from 161° C. with brown coloration.

IR (KBr): ν=1730, 1650, 1550, 1250, 1055, 1020, 930, 810 cm$^{-1}$ $^1$H-NMR (D$_2$O): δ 1.0–2.2 (m, 9H, with t at 1.31, 7 Hz); 3.30 (m, 2H); 3.9–4.8 (m with H$_2$O signal at 4.68 as int. std.); 4.8–5.3 (m, 10H)

$^{13}$C-NMR (D$_2$O): δ 15.94; 29.68; 30.54; 33.17; 41.87; 55.93; 65.19; 68.23; 68.53; 69.04; 74.36; 77.33; 79.81; 78.45; 78.80; 79.61; 80.47; 103.36; 103.99; 171.39; 171.65; 176.12

EXAMPLE 37

N,N'-1,3-Propanediylbis-D-gulonamide 3.56 g of D-gulono-γ-lactone and 0.84 ml of 1,3-diaminopropane are dissolved in 40 ml of dimethylformamide and the mixture is stirred for 6 hours at 60° C. The mixture is then stirred into 200 ml of isopropanol and the precipitate is washed with isopropanol and diethyl ether. The solid is dissolved in 20 ml of dimethylformamide and precipitated again using 200 ml of isopropanol. The precipitate is dissolved in water and freezedried. 2.2 g of a colorless powder are obtained.

Melting point: 49°–54° C. with sintering, 168° C. with decomposition

IR (KBr): ν=2930, 2890, 1645, 1545, 1440, 1080 cm$^{-1}$ $^1$H-NMR (D$_2$O): δ 1.74 (dt, 2H, 6.5 Hz); 3.27 (t, 4H, 6.5 Hz); 3.45–4.05 (m, 10H); 4.23 (d, 2H, 6 Hz); 4.68 (H$_2$O, int. std.)

$^{13}$C-NMR (D$_2$O): δ 30.65; 39.02; 65.13; 72.64; 74.69; 75.00; 75.12; 176.78; int. std. CH$_3$OH δ 51.56

EXAMPLE 38

N,N'-1,2-Propanediylbis-D-galactonamide 4.1 g of the title compound as colorless powder are obtained analogously to Example 37 from 7.12 g of D-galactono-γ-lactone and 1.48 g of 1,2-diaminopropane.

Melting point: 183°–193° C. with decomposition and brown coloration

IR (KBr): ν=2940, 1656, 1552, 1109, 1055, 1044, 1028, 865 cm$^{-1}$ $^1$H-NMR (D$_2$O): δ 1.18 (d, 3H, 6 Hz); 3.1–4.6 (m, 15H); 4.68 (H$_2$O, int. std.)

$^{13}$C-NMR (D$_2$O): δ 19.64; 19.77; 46.16; 47.87; 48.10; 65.90; 71.93; 72.64; 73.49; 177.75; 178.42; 178.54

EXAMPLE 39

N,N'-1,4-Butanediylbis-L-mannonamide 2.4 g of the title compound are obtained as colorless powder analogously to Example 18 from 3.56 g of L-mannono-γ-lactone and 0.90 g of putrescine.

Decomposition from 181°–188° C. with brown coloration

IR (KBr): ν=2955, 2925, 2855, 1643, 1555, 1231, 1098, 1043, 1031, 880, 740, 640 cm$^{-1}$

¹H-NMR (D₂O): δ 1.58 (m, 4H); 3.30 (m, 4H); 3.75 (m, 8H); 4.02 (d, 2H, 7 Hz); 4.26 (d, 2H, 7 Hz); 4.68 (H₂O int. std.)

¹³C-NMR (D₂O): δ 28.42; 41.38; 65.67; 72.58; 72.76; 73.43; 75.19; 177.09,

EXAMPLE 40

N,N'-Dilactobionoylhydrazine 6.1 g of crude product are obtained analogously to Example 37 from 6.8 g of lactobiono-1,5-lactone and 0.5 ml of hydrazine hydrate. Column chromatography over Fractogel TSK HW 40S yields the pure product as a colorless powder after freeze-drying.

EXAMPLE 41

Decasodium N,N'-1,3-propanediylbis(2,3,4,5,6-penta-O-sulfo-D-gulonamide)

9.8 g of crude or 6.4 g of pure product as colorless powder are obtained analogously to Example 18 from 2.2 g of N,N'-1,3-propanediylbis-D-gulonamide and 12.3 g of pyridine-sulfur trioxide complex.

Decomposition from 185° C. with brown coloration.

IR (KBr): ν=2960, 1675, 1555, 1250, 1070, 1010, 925, 805 cm⁻¹

¹H-NMR (D₂O): δ 1.85 (m, 2H); 3.34 (m, 4H); 4.52 (d, 4H, 3.5 Hz); 5.07 (m, 6H); 5.34 (d, 2H, 3.5 Hz); 4.68 (H₂O, int. std.)

¹³C-NMR (D₂O): δ 30.05; 39.62; 68.78; 76.28; 76.41; 77.78; 80.14; 171.15; int. std. CH₃OH δ 51.55

EXAMPLE 42

Decasodium N,N'-1,2-propanediylbis(2,3,4,5,6-penta-O-sulfo-D-galactonamide)

13.0 g of crude or 9.8 g of pure product as colorless powder are obtained analogously to Example 18 from 3.3 g of N,N'-1,2-propanediylbis-D-galactonamide and 19.5 g of pyridine-sulfur trioxide complex.

Decomposition from 191° C. with brown coloration.

IR (KBr): ν=2970, 1665, 1550, 1250, 1065, 1040, 1007, 900 cm⁻¹

¹H-NMR (D₂O): δ 1.26 (d, 3H, 6.5 Hz); 2.9–4.3 (m, 3H); 4.3–4.6 (m, 4H); 4.68 (H₂O, int. std.); 4.8–5.3 (m, 8H)

¹³C-NMR (D₂O): δ 19.20; 45.94; 46.15; 47.61; 69.07; 78.42; 78.86; 79.90; 170.84; 711.03; 191.93 int. std. CH₃OH δ 51.57

EXAMPLE 43

Decasodium N,N'-1,4-butanediylbis(2,3,4,5,6-penta-O-sulfo-L-mannonamide)

10.5 g of crude or 7.2 g of pure product as colorless powder are obtained analogously to Example 18 from 2.5 g of N,N'-1,4-butanediylbis-L-mannonamide and 14.1 g of pyridine-sulfur trioxide complex.

Decomposition from 180° C. with brown coloration

IR (KBr): ν=2960, 2930, 2850, 1670, 1555, 1250, 1075, 1010, 925 cm⁻¹

¹H-NMR (D₂O): δ 1.65 (m, 4H); 3.31 (m, 4H); 4.43 (m, 4H); 4.8–5.08 (m, 4H); 5.15 (m, 4H); 4.68 (H₂O, int. std.)

¹³C-NMR (D₂O): δ 27.98; 41.62; 69.15; 78.81; 79.36; 79.75; 170.93; int. std. CH₃OH δ 51.55

EXAMPLE 44

Hexadecasodium N,N'-bis-[2,3,5,6-tetra-O-sulfo-4O-(2,3,4,6-tetra-O-sulfo-β-D-galactopyranosyl)-gluconoyl]hydrazine 17.5 g of crude or 7.3 g of pure product are obtained analogously to Example 18 from 6.0 g of N,N'-dilactobionoylhydrazine and 33.7 g of pyridine-sulfur trioxide complex.

EXAMPLE 45

5.000 kg of hexadecasodium N,N'-1,3-propanediylbis-[2,3,5,6-tetra-O-sulfo-4-O-(2,3,4,6-tetra-O-sulfo-β-D-galactopyranosyl)-D-gluconamide]as dry substance are dissolved with stirring in 40 liters of water for injection. After adjusting the pH of the solution to 7.5 with dilute sodium hydroxide solution, it is made up to 50.00 liters of water for injection and filtered through a membrane filter of pore size 0.2 μm. The solution is filtered off under aseptic conditions into ampoules of 1 ml and these are sealed off.

I claim:

1. Polysulfuric acid exters of bisaldonamides an their derivatives of the formula (I):

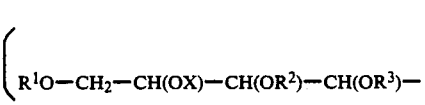

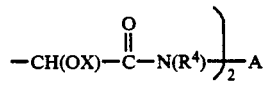

in which either all radicals R¹, R² and R³ independently of one another represent X, or two of the radicals R¹, R² and R³ stand for X, and the third stands for a radical of the formulae (II) to (VII),

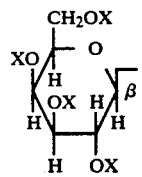

(II)

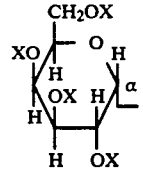

(III)

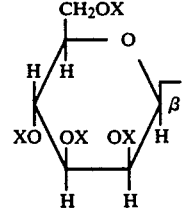

(IV)

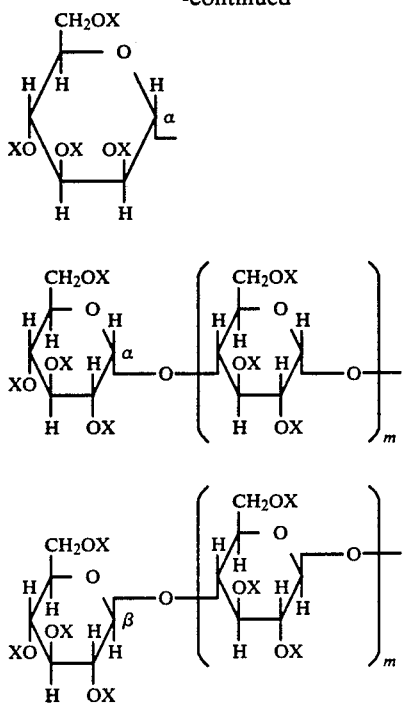

wherein

X in the formulae (I) to (VII) represents independently a hydrogen atom or the group —SO$_3$H, wherein at least one X represents the group —SO$_3$H, m stands for 0, 1, 2, 3, 4, 5 or 6, A in formula (I) represents a straight-chain or branched, saturated alkylene radical having 2 to 22 carbon atoms which is unsubstituted or substituted by one or more radicals —CO$_2$R$^5$, or A stands for a single bond or the radical

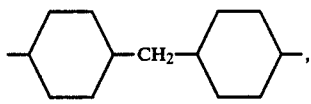

R$^4$ and R$^5$ independently represent a hydrogen atom or a C$_1$-C$_6$-alkyl radical, and their salts of inorganic or organic bases.

2. Compounds as claimed in claim 1, wherein the saturated alkylene radical having 2 to 22 carbon atoms which is unsubstituted or substituted by one or more radicals —CO$_2$R$^5$ is interrupted by up to five —O—, —S—, —S—S—, —S(O)$_n$—,

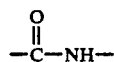

and/or —NR$^6$— groups or cycloalkylene radicals or arylene radicals, wherein R$^5$ and R$^6$ independently represent a hydrogen atom or a C$_1$-C$_6$-alkyl radical and n is 1 or 2.

3. Compounds as claimed in claim 1 or 2, wherein in the formulae (1) to (VII) at least half the X group represent an —SO$_3$H group 4. Compound as claimed in claim 3, wherein each X in said formulae represents the group —SO$_3$H.

5. Compounds as claimed in claim 1 or 2, wherein R$^2$ and R$^3$ represent X.

6. Compounds as claimed in claim 5, wherein R$^1$ represents the radical (III) or the radical (VI) and m=0.

7. Compounds as claimed in claim 5, wherein A in formula (I) represents a polymethylene radical —(CH$_2$)$_p$— and p=2 to 12.

8. Compounds as claimed in claim 1 or 2, wherein R$^1$ and R$^3$ represent X.

9. Compounds as claimed in claim 8, wherein R$^2$ represents the radical (II) or the radical (VI) and m=0 or the radical (VII) and m=0.

10. Compounds as claimed in claim 8, wherein A in formula (I) represents a polymethylene radical —(CH$_2$)$_p$— and p=2 to 22.

11. Compounds as claimed in claim 10, wherein p=2 to 12.

12. Compounds as claimed in claim 10, wherein A in formula (I) is substituted by one, two or more radicals —CO$_2$R$^5$, and where R$^5$ represents a hydrogen atom or a C$_1$-C$_6$-alkyl radical.

13. A process for the preparation of polysulfuric acid esters of bis-aldonamides and their derivatives of the formula (I) as claimed in claims 1 or 2, wherein bis-aldonamides of the formula (IX):

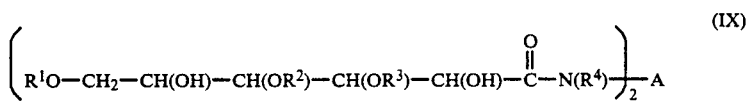

in which either all radicals R$^1$, R$^2$ and R$^3$ independently of one another represent hydrogen, or two of the radicals R$^1$, R$^2$ and R$^3$ represent hydrogen, and the third represents a radical of the formulae (II) to (VII):

-continued

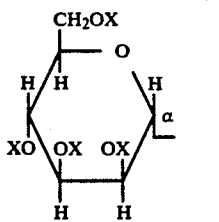
(V)

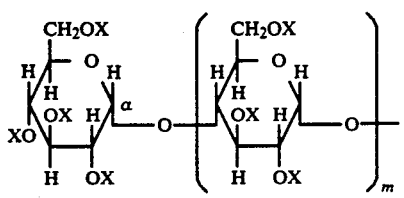
(VI)

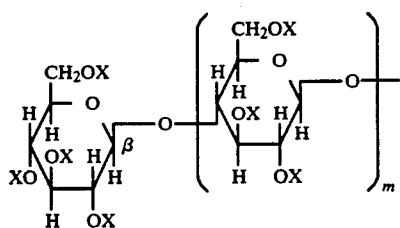
(VII)

wherein A is as defined above, $R^4$ and $R^5$ represent a hydrogen atom or a $C_1$-$C_6$-alkyl radical, and X in the formulae (II) to (VII) represents a hydrogen atom, are reacted with a sulfating agent in an aprotic solvent.

14. The process as claimed in claim 13, wherein in each case, without isolation of intermediates, aldonic acids of the formula (VIII):

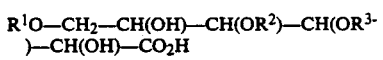
(VIII)

in which either all radicals $R^1$, $R^2$ and $R^3$ independently of one another represent hydrogen, or two of the radicals $R^1$, $R^2$ and $R^3$ represent hydrogen, and the third represents a radical of the formulae (II) to (VII):

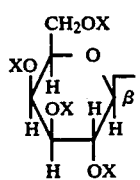
(II)

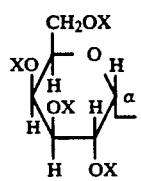
(III)

-continued

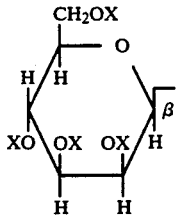
(IV)

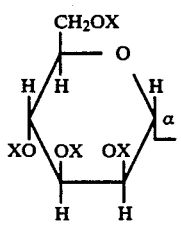
(V)

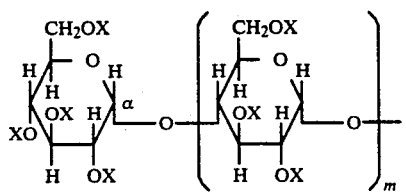
(VI)

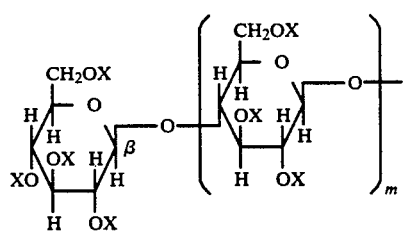
(VII)

X in the formulae (II) to (VII) represents a hydrogen atom, are converted into the aldonamides of the formula (IX) and reacted to give their polysulfuric acid esters.

15. The process as claimed in claim 13, further comprising the step of converting the products obtained by the reaction of the bis-aldonamides of formula (IX) into the corresponding salts using an inorganic or organic base.

16. Compounds as claimed in claim 2, wherein A in formula represents a straight chain alkylene radical having 2 to 22 carbon atoms, whose chain can be interrupted by the groups —O—, —S—, —S—S—, —S(O)$_n$—,

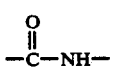

and/or —NR$^6$ or cycloalkylene radicals or arylene radicals, wherein n is 1 or 2, $R^1$ and $R^3$ represent X and $R^6$ represents a hydrogen atom or a $C_1$-$C_6$-alkyl radical.

17. Medicaments, containing one or more compounds of the formula (I), as claimed in claims 1 or 2, and pharmaceutically acceptable excipients and auxiliaries.

* * * * *